US010456364B2

(12) United States Patent
Struck et al.

(10) Patent No.: US 10,456,364 B2
(45) Date of Patent: *Oct. 29, 2019

(54) USE OF PROCALCITONIN (PCT) IN RISK STRATIFICATION AND PROGNOSIS OF PATIENTS WITH A PRIMARY, NON-INFECTIOUS DISEASE

(75) Inventors: Joachim Struck, Berlin (DE); Andreas Bergmann, Berlin (DE)

(73) Assignee: B.R.A.H.M.S. GmbH, Henningsdorf (DE)

(*) Notice: Subject to any disclaimer, the term of this patent is extended or adjusted under 35 U.S.C. 154(b) by 1344 days.

This patent is subject to a terminal disclaimer.

(21) Appl. No.: 13/034,752

(22) Filed: Feb. 25, 2011

(65) Prior Publication Data

US 2011/0152170 A1 Jun. 23, 2011

Related U.S. Application Data

(62) Division of application No. 12/671,702, filed as application No. PCT/EP2008/060176 on Aug. 1, 2008, now abandoned.

(30) Foreign Application Priority Data

Aug. 3, 2007 (EP) .................................... 07015271
Mar. 12, 2008 (EP) .................................... 08152651

(51) Int. Cl.
| | | |
|---|---|---|
| G01N 31/00 | (2006.01) | |
| G01N 33/53 | (2006.01) | |
| A61K 31/00 | (2006.01) | |
| G01N 33/68 | (2006.01) | |
| G01N 33/74 | (2006.01) | |

(52) U.S. Cl.
CPC ......... *A61K 31/00* (2013.01); *G01N 33/6893* (2013.01); *G01N 33/74* (2013.01); *G01N 2333/585* (2013.01)

(58) Field of Classification Search
CPC ...... A61K 31/43; A61K 31/545; A61K 35/74; C07K 16/18; C07K 16/26; G01N 33/53; G01N 33/543; G01N 33/569; G01N 33/577; G01N 33/6893; G01N 33/74; G01N 33/78; G01N 2333/58; G01N 2333/585; G01N 2469/00; G01N 2800/26; G01N 2800/32; G01N 2800/50; G01N 2800/52
USPC ........... 435/4, 7.1, 7.32, 7.94, 973; 436/518, 436/524, 528, 64, 87, 172, 811, 817; 530/387.9, 388.24, 388.25, 388.7, 389.2, 530/389.3, 389.6, 391.1, 391.3; 424/9.2; 514/1.4, 2.4
See application file for complete search history.

(56) References Cited

U.S. PATENT DOCUMENTS

| | | | |
|---|---|---|---|
| 5,993,811 A * | 11/1999 | Becker | C07K 16/26 424/130.1 |
| 7,361,473 B2 | 4/2008 | Valkirs et al. | |
| 8,383,332 B2 * | 2/2013 | Bergmann | G01N 33/56911 435/4 |
| 8,465,941 B2 * | 6/2013 | Bergmann | G01N 33/74 435/15 |
| 2004/0253637 A1 * | 12/2004 | Buechler et al. | 435/7.1 |
| 2007/0212742 A1 * | 9/2007 | Bergmann et al. | 435/7.93 |
| 2010/0036542 A1 | 2/2010 | Karte | |
| 2011/0136161 A1 | 6/2011 | Struck et al. | |
| 2011/0263438 A1 | 10/2011 | Soylemez | |

FOREIGN PATENT DOCUMENTS

| | | |
|---|---|---|
| EP | 2154587 A2 | 2/2010 |
| WO | WO 2008/040328 | 4/2008 |

OTHER PUBLICATIONS

Assicot et al., 1993. High serum procalcitonin concentrations in patients with sepsis and infection. The Lancet 341: 515-518.*
Hoksch et al., Jan. 2007. Procalcitonin and brain natriuretic peptide as parameters in the postoperative course of patients with major pulmonary resection. Interact. CardioVasc. Thoracic Surg. 6: 155-159.*
Smith et al., 1995. Elevated serum procalcitonin levels in patients with melioidosis. Clin. Inf. Dis. 20: 641-645.*
Gendrel et al., 1997. Measurement of procalcitonin levels in children with bacterial or viral meningitis. Clin. Inf. Dis. 24: 1240-1242.*
Piechota et al., 2006. N-terminal brain natriuretic propeptide levels correlate with procalcitonin and C-reactive protein levels in septic patients. Cellular & Molecular Biology Letters 12: 162-175.*
Soylemez et al., 2006. A novel mechanism between diabetes mellitus complications and procalcitonin gene expression. Molecular Therapy 13 (Suppl. 1): S86, Abstract #225.*
Viallon et al., 2005. Decrease in serum procalcitonin levels over time during treatment of acute bacterial meningitis. Critical Care 9: R344-R350.*
Cheng et al., 2005. Melioidosis: epidemiology, pathophysiology, and management. Clin. Microbiol. Rev. 18: 383-416.*
Christ-Crain et al. (The Lancet 363: 600, 2004).*
Hoksch et al. (Interact. CardioVasc. Thoracic Surg. 6: 155, Jan. 2007).*
Jimeno et al. (Cancer 100: 2462, 2004).*
Morgenthaler reference of record (Clin.Chenn. 48(5):788-790,2002.*
Substantive Action from corresponding EPO Application No. 08 786 791.7. Dated: May 4, 2010. Communication pursuant to Article 94(3) EPC.

(Continued)

*Primary Examiner* — Lisa V Cook
(74) *Attorney, Agent, or Firm* — Millen White Zelano and Branigan, PC; John Sopp (57) ABSTRACT

Subject of the present invention are assays and in vitro methods for the in vitro diagnosis, prognosis and risk stratification of a patient having a primary, non-infectious disease, whereby the level of Procalcitonin (PCT) in a sample of a body fluid of the patient is indicative for the risk of the patient to contract a further disease or medical condition.

34 Claims, 2 Drawing Sheets

(56) References Cited

OTHER PUBLICATIONS

Applicant's amended claims pursuant to Article 94(3) EPC dated May 4, 2010 in corresponding EPO Application No. 08 786 791.7. Applicant's communication dated Sep. 3, 2010.
Applicant's amended claims and basis for the amendments according to Article 123(2)EPC in corresponding EPO Application No. 08 786 791.7. Applicant's communication dated Oct. 19, 2010.
Substantive Action from corresponding EPO Application No. 08 786 791.7. Dated: Dec. 30, 2010. Communication under Rule 71(3) EPC.
Remskar et al. "Procalcitonin in patients with acute myocardial infarction" Wiener Klinische Wochenschrift 114:5-6:205-210 (2002).
Kitanovski et al. "Diagnostic accuracy of procalcitonin and interleukin-6 values for predicting bacteremia and clinical sepsis in febrile neutropenic children with cancer" Eur J. Clin. Microbiol Infect Dis. 25:413-415 (2006).
Carsin et al. "Evolution and significance of circulating procalcitonin levels compared with IL-6, TNFα and endotoxin levels early after thermal injury" Burns, 23(3):218-224 (1997).
Husova et al. "Prokalcitonin jako indikator infekce u pacientu s jaterni cirhozou" Vnitr Lek. 50(2):153-156 (2004).
Prieto et al. "Plasma procalcitonin measured by time-resolved amplified cryptate emission (TRACE) in liver transplant patients. A prognosis marker of early infectious and non-infectious postoperative complications" Clin Chem Lab Med. 46(5):660-686 (2008).
Morgenthaler et al. "Sensitive immunoluminometric assay for the detection of procalcitonin", Clinical Chemistry 48(5):788-790 (2002).
Reith et al. "Procalcitonin in early detection of postoperative complications" Digestive Surgery 15:260-265 (1998).
Pelosi et al. "Prognostic role of clinical and laboratory criteria to identify early ventilator-associated pneumonia in brain injury" Chest Journal 134(1):101-108 (Jul. 2008).
Jimeno et al. "Assessment of procalcitonin as a diagnostic and prognostic marker in patients with solid tumors and febrile neutropenia" Cancer 100(11): 2462-2469 (Jun. 1, 2004).
Christ-Crain et al. "Effect of procalcitonin-guided treatment on antibiotic use and outcome in lower respiratory tract infections: cluster-randomised, single-blinded intervention trial" The Lancet 363:600-607 (2004).
Monagle et al. "An increase in serum procalcitonin over twenty-four hours predicts the clinical outcome of children admitted with febrile neutropenia" Abstract # 4583.
Briel et al. "Procalcitonin-guided antibiotic use versus a standard approach for acute respiratory tract infections in primary care: study protocol for a randomized controlled trial and baseline characteristics of participating general practitioners [ISRCTN73182671]" BMC Family Practice 6(34):1-8 (2005).
Schuetz et al. "Procalcitonin guided antibiotic therapy and hospitalization in patients with lower respiratory tract infections: a prospective, multicenter, randomized controlled trial" BMC Health Services Research 7(102):1-9 (2007).
Sandek et al. "Procalcitonin guided antibiotic treatment in heart failure" The Lancet 363:1555 (May 8, 2004).
International Search Report completed Feb. 11, 2009. International Application No. PCT/EP2008/060176. International Filing Date: Aug. 1, 2008. International Publication No. WO 2009/019230. International Publication Date: Feb. 12, 2009.
Richards, A. M., et al., "Plasma N-Terminal Pro-Brain Natriuretic Peptide and Adrenomedullin: New Neurohormonal Predictors of Left Ventricular Function and Prognosis After Myocardial Infarction," Circulation—Journal of the American Heart Association, 1998; 97; 1921-1929—Downloaded from circ.ahajournals.org on Jan. 19, 2010.
Qi, Y. F., et al., "Effects of Different Peptide Fragments Derived from Proadrenomedullin on Gene Expression of Adrenomedullin Gene," Peptides 23 (2002) 1141-1147.
Opposition decision EP2293076 (app# 10188289.2) dated Aug. 26, 2014 (pp. 1-5).
Examination report in corresponding In 206/MUMNP/2010 dated Jan. 10, 2014 (pp. 1-4).
Pelosi Paolo et al: "Prognostic role of clinical and laboratory criteria toidentify early ventilator-associated pneumonia in brain injury" Chest, The College, Chicago, IL, US, vol. 134, No. 1, Jul. 1, 2008 (Jul. 1, 2008), pp. 101-1 08, XP008099400 ISSN: 0012-3692.
Monagle Paul et al: "An increase in serum procalcitonin over twenty-four hours predicts the clinical outcome of children admitted with febrile neutropenia" Blood, American Society of Hematology, US, vol. 98, No. 11 part 2, Nov. 16, 2001 Nov. 16, 2001), p. 217b, X POO8101787 ISSN: 0006-4971.
(NK17) Muller et al: International Journal of Antimicrobial Agents 30S (2007). pp. 516-523.
(NK16-03) Nylen et al; Correspondence—CID 2003:36 (Mar. 15) pp. 823-824.
(NK15) Becker et al: Crit Care Med 2008: vol. 36, No. 3; pp. 27-39.
Christ-Crain M et al: "Effect of procalcitonin-guided treatment on antibiotic use and outcome in lower respiratory tract infections: clusterrandomised, single-blinded intervention trial" Lancet, Lancet Limited. London, GB, vol. 363, No. 9409, Feb. 21, 2004 (Feb. 21, 2004), pp. 600-607 (NK7).
Christ-Crain M et al: American Journal of Rspiratory and Critical Care Medicine Vo. 174 (2006) pp. 85-93 (NK8).
Stolz et al: Chest 2007;131: pp. 9-19 (NK12-03).
Christ-Crain M et al: Swiss Med Wkly 2005:135:pp. 451-460 (NK12).
Assicot et al: The Lancet, vol. 341: Feb. 27, 1993; pp. 515-519 (nk13-03).
Gendrel et al: CID 1997; 24 (Jun.) pp. 1240-1242 (NK14-03).
(NK15-03) Koksal et al: The Turkish Journal of Pediatrics 2007; 49; pp. 21-29.
Soylemez et al. European Journal of Human Genetics vol. 18, No. Suppl. 1, Jun. 12, 2010 pp. 352.
Soylemez et al. Molecular Therapy, vol. 11, Aug. 15, 2005, pp. 346.

* cited by examiner

USE OF PROCALCITONIN (PCT) IN RISK STRATIFICATION AND PROGNOSIS OF PATIENTS WITH A PRIMARY, NON-INFECTIOUS DISEASE

This application is a divisional of U.S. Ser. No. 12/671,702, filed Feb. 2, 2010, now abandoned.

Subject of the present invention is the in vitro diagnosis, prognosis and risk stratification of a patient having a primary, non-infectious disease, whereby the level of Procalcitonin (PCT) in a sample of a body fluid of the patient is indicative for the risk of the patient to contract a further disease or medical condition.

BACKGROUND OF THE INVENTION

Procalcitonin (PCT) has become a well-established biomarker for sepsis diagnosis: PCT reflects the severity of bacterial infection and is in particular used to monitor progression of infection into sepsis, severe sepsis, or septic shock. PCT concentrations in sepsis, severe sepsis, or septic shock are typically above 1 ng/mL. It is possible to use PCT to measure the activity of the infection-associated systemic inflammatory response, to control success of therapy, and to estimate prognosis (Assicot M et al.: High serum procalcitonin concentrations in patients with sepsis and infection. Lancet 1993, 341:515-8; Clec'h C et al.: Diagnostic and prognostic value of procalcitonin in patients with septic shock. Crit Care Med 2004; 32:1166-9; Lee Y J et al.: Predictive comparisons of procalcitonin (PCT) level, arterial ketone body ratio (ABR), APACHE III score and multiple organ dysfunction score (MODS) in systemic inflammatory response syndrome (SIRS), Yonsei Med J 2004, 45, 29-37; Meisner M.: Biomarkers of sepsis: clinically useful? Curr Opin Crit Care 2005, 11, 473-480; Wunder C et al.: Are IL-6, IL-10 and PCT plasma concentrations reliable for outcome prediction in severe sepsis? A comparison with APACHE III and SAPS II. Inflamm Res 2004, 53, 158-163). The increase of PCT levels in patients with sepsis correlates with mortality (Oberhoffer M et al.: Outcome prediction by traditional and new biomarkers of inflammation in patients with sepsis. Clin Chem Lab Med 1999; 37:363-368).

An increasing number of studies discusses the potential role of PCT in non-septic infectious diseases like pneumonia, bacterial meningitis and malaria (Bugden S A et al.: The potential role of procalcitonin in the emergency department management of febrile young adults during a sustained meningococcal epidemic. Emerg Med Australas 2004, 16, 114-119; Chiwakata C B et al.: Procalcitonin as a parameter of disease severity and risk of mortality in patients with *Plasmodium falciparum* malaria. J Infect Dis 2001, 183, 1161-1164; Schwarz S et al.: Serum procalcitonin levels in bacterial and abacterial meningitis, Crit Care Med 2000, 28, 1828-1832).

In vitro-studies showed that PCT plays an important role during monocyte adhesion and migration and further has an effect on inducible nitric oxide synthase (iNOS) gene expression (Linscheid P et al.: Expression and secretion of procalcitonin and calcitonin gene-related peptide by adherent monocytes and by macrophage-activated adipocytes, Crit Care Med 2004, 32, 1715-1721; Wiedermann F J et al.: Migration of human monocytes in response to procalcitonin, Crit Care Med, 2002, 30, 1112-1117; Hoffmarm G et al.: Procalcitonin amplifies inducible nitric oxide synthase gene expression and nitric oxide production in vascular smooth muscle cells, Crit Care Med, 2002, 30, 2091-2095.).

PCT has been used to guide antibiotic therapy (Christ-Crain M et al.: Effect of procalcitonin-guided treatment on antibiotic use and outcome in lower respiratory tract infections: cluster-randomised, single-blinded intervention trial, Lancet. 2004 Feb. 21; 363(9409):600-7.): In patients with symptoms of lower respiratory tract infections presenting at the emergency department PCT was measured, and only patients with PCT concentrations >0.25 ng/mL or >0.5 ng/mL were treated with antibiotics. Apparently, this regimen led to a clinical outcome undistinguishable from the control group, in which also many patients with PCT concentrations <0.25 ng/mL received antibiotics. Of note, in this study, patients with relevant comorbidities as for instance heart failure were excluded. Thus, it is unclear so far, whether the presence of a primary disease in addition to an infection should influence the interpretation of PCT concentrations below 0.25 ng/mL. A relevant primary disease might put an additional burden on the immune system, and biomarkers of infection, such as PCT, in such situation might be indicative of an infection in a different, i.e. lower, concentration range than in the absence of a relevant primary disease.

In healthy individuals, the PCT concentration is well below 0.25 ng/mL: The median concentration has been determined to be 0.014 ng/mL (Morgenthaler N G et al.: Sensitive immunoluminometric assay for the detection of procalcitonin. Clin Chem. 2002 May, 48(5):788-90.)

A method for diagnosis of infections or inflammatory diseases of the airways and lungs with associated heart failure, wherein the biomarker procalcitonin is determined in a patient, is described in WO 2008/040328 A2.

SUMMARY OF THE INVENTION

The present invention is based on the surprising finding that in samples of patients with a primary, non-infectious disease, slightly elevated procalcitonin (PCT) levels (concentrations) have been detected at a large frequency and are of diagnostic relevance. Remarkably, the inventors have identified a large number of samples having serum levels above 0.03 ng/mL (26.0%) and 0.05 ng/mL (14.7%), respectively, from a total of 4997 samples of patients having a primary, non-infectious disease. Slightly elevated PCT levels relate to PCT levels in the range of from about 0.02 to 0.25 ng/mL, preferably between about 0.02 and 0.1 ng/mL. The presence of slightly elevated PCT levels may be indicative for the risk of a patient having a non-infectious primary disease to acquire a yet clinically unmanifested and/or yet asymptomatic further disease or medical condition. Such a further disease or medical condition may be related to a local infection or the local infection may facilitate, accelerate and/or enhance the risk of contracting or acquiring the further disease or medical condition. The present invention provides a method for the prognosis of a patient's risk to acquire a further disease or medical condition in addition to an non-infectious primary disease. This also allows for adaption of the treatment of these patients, e.g. by an additional antibiotics therapy which the patient would not have necessarily received if the elevated PCT level had not been detected. It has to be noted that so far, patients with non-infectious primary diseases are not routinely screened for their PCT levels during diagnosis. It is taught by the present invention that patients with a primary disease not being an infection should be assayed for their PCT level to allow for the prognosis of the risk to acquire a further disease or medical condition and ultimately to allow for the adaption of therapy.

Hence, the present invention provides an in vitro method for prognosis for a patient having a primary disease not being an infection, the method comprising: determining the level of procalcitonin or fragments thereof of at least 12 amino acids in length, preferably more than 50 amino acids in length, more preferably more than 110 amino acids in length, in a sample obtained from said patient; and correlating said level of procalcitonin or fragments thereof to a risk of the patient to contract a further disease or medical condition which has not yet been manifested and/or is not yet symptomatic.

DETAILED DESCRIPTION OF THE INVENTION

The present invention relates to an in vitro method for prognosis for a patient having a primary disease not being an infection, the method comprising: determining the level of procalcitonin or fragments thereof of at least 12 amino acids in length, preferably more than 50 amino acids in length, more preferably more than 110 amino acids in length, in a sample obtained from said patient; and correlating said level of procalcitonin or fragments thereof to a risk of the patient to contract a further disease or medical condition which has not yet been manifested and/or is not yet symptomatic.

"Patients" in the meaning of the invention are understood to be all persons or animals, irrespective whether or not they exhibit pathological changes, unless stated otherwise. In a preferred embodiment the patient according to the invention is a human.

Preferably, the patient in the context of the present invention has a primary disease not being an infection and the level of procalcitonin or fragments thereof of at least 12 amino acids in length, in serum or plasma samples of said patient is below 0.25 ng/mL.

In the present invention, the term "prognosis" denotes a prediction of how a subject's (e.g. a patient's) medical condition will progess. This may include an estimation of the chance of recovery or the chance of an adverse outcome for said subject.

As mentioned heroin in the context of proteins or peptides, the term "fragment" refers to smaller proteins or peptides derivable from larger proteins or peptides, which hence comprise a partial sequence of the larger protein or peptide, Said fragments are derivable from the larger proteins or peptides by saponification of one or more of its peptide bonds.

Procalcitonin is a 116 amino acids comprising peptide. Smaller variants, such as for instance PCT 3-116 and others, exist as well. Thus the length of procalcitonin fragments is at least 12 amino acids, preferably more than 50 amino acids, more preferably more than 110 amino acids.

Preferably herein, said risk of contracting a further disease or medical condition is related to an existing bacterial infection, particularly a local infection. A local infection may facilitate, accelerate and/or enhance the risk of contracting or acquiring a further disease or medical condition in a patient having a non-infectious primary disease.

In particularly preferred embodiments of the in vitro method, said level of procalcitonin or fragments thereof is indicative for a bacterial infection in the patient.

It is further preferred that said infection is a local infection.

A local infection herein relates to all infections being less severe than a sepsis. A sepsis is defined as an infection being associated with the "Systemic Inflammatory Response Syndrome" ("SIRS") (Levy M M et al. 2001 SCCM/ESICM/ACCP/ATS/SIS International Sepsis Definitions Conference. Crit Care Med. 2003 April; 31(4):1250-6).

The local infection may for example be an infection in the oral cavity, at the teeth or the root of the teeth, infection in wounds, infection in the respiratory tract, or haemorrhoids, or others.

Said local infection herein may be treated by administration of an antibiotic. Treatment of the local infection leads to a decreased risk of the patient for acquiring the further disease or medical condition. Hence, in a preferred embodiment of the in vitro method, said bacterial infection is treatable with an antibiotic. In this case it is preferred, that the risk of contracting a further disease or medical condition decreases when the patient is treated with an antibiotic.

The correlating step of the in vitro method of the present invention preferably comprises comparing said level of procalcitonin or fragments thereof to a threshold level, whereby, when said level of procalcitonin or fragments thereof exceeds said threshold level, said patient is predisposed to said risk.

Figure 1:
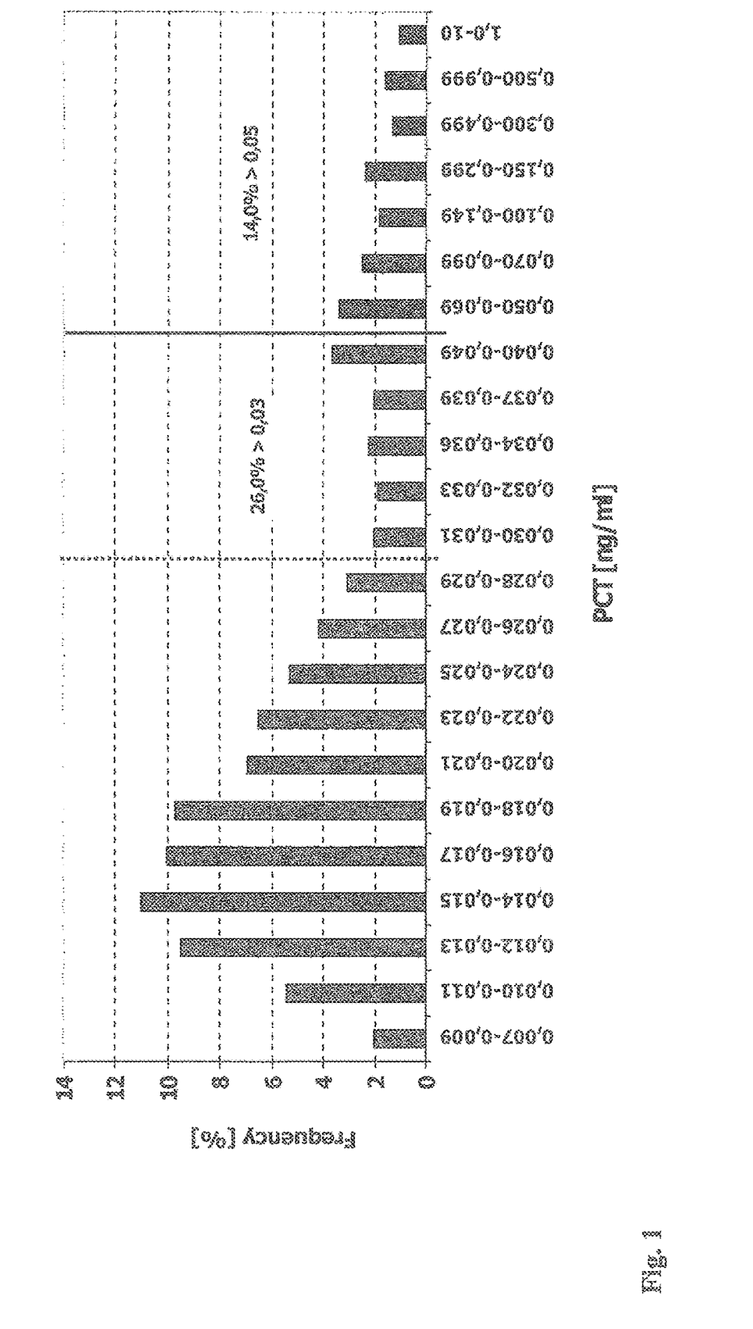
FIG. 1 shows a histogram plot of the frequency of procalcitonin level ranges in patients' samples. These were 4997 unselected samples consecutively sent by physicians of various specialties to a private laboratory for various types of analysis, but not PCT.

Said threshold level is preferably between 0.02 and 0.25 ng/mL, more preferably between 0.02 and 0.1 ng/mL, even more preferably at about 0.05 (+/−0.01) ng/mL, and most preferably at about 0.03 (+/−0.01) ng/mL. Definition of these threshold levels comes from the analysis of the frequency distribution of PCT level ranges shown in the histogram of appended FIG. 1 and Example 1.

In a particular embodiment said primary disease is not arteriosclerosis. In another embodiment said primary disease is not heart failure. It is in some embodiments of the invention said primary disease is not an acute coronary syndrome. Furthermore, it is in a particular embodiment preferred that said primary disease is not a coronary disease. In a particular embodiment the further disease or medical condition is not selected from the group comprising acute coronary syndrome, heart failure or myocardial infarction.

In one embodiment said further disease or medical condition is not an infection, particularly not an infection of the airways and lungs.

In another embodiment of the in vitro method according to the invention, said primary disease is selected from but not restricted to the group comprising cancer, diabetes, chronic gastrointestinal diseases, chronic renal diseases, hypertension, orthopaedic diseases including osteoporosis, and neurodegenerative diseases including Alzheimer's disease.

Furthermore, in another embodiment said further disease or medical condition is selected from the group comprising cardiological diseases selected from but not restricted to the group comprising atherosclerosis, acute coronary syndromes and heart failure.

The primary disease herein relates to a disease which is already manifested and/or is already symptomatic. The further disease or medical condition relates to a disease which is not yet manifested and/or is not yet symptomatic.

The sample from the patient may for example be selected from the group comprising a blood sample, a serum sample, a plasma sample, and an urine sample or an extract of any of the aforementioned samples.

In a particular embodiment of the invention, the in vitro method further comprises mathematically combining said level of procalcitonin or fragments thereof with the level of one or more additional prognostic biomarkers, whereby the combination of said level of procalcitonin or fragments thereof with said level of additional prognostic biomarker(s) increases the predictive value of said level of procalcitonin or fragments thereof or the level of said related biomarker for said risk of contracting a further disease or medical condition.

In the context of the present invention, an "algorithm" or "mathematical algorithm" refers to the use of a mathematical or statistical method or model used to compare a certain measured value with values of a reference population in order to stratify said measured value. This may for instance be the median of the level of a certain entity in an ensemble of pre-determined samples, which means that the measured level of said entity is compared with the mathematical median of the level of said entity in a given number of samples. The number of samples used to determine the median is not particularly limited, but should be sufficient in order to ensure statistical significance of the median. The number of samples used to determine the median may even increase over the course of time, as the results of further measurement values from clinical samples are added in order to increase the statistic significance of the median. Preferably, the sample number is chosen such that statistical significance of the median is ensured. Thus, said median is used as a reference value, whereby the measured level of the aforementioned entity can be statistically correlated with a certain physiological state, e.g. the propensity of an adverse outcome for a patient, depending on the relative level above or below the median and the extent of deviation of the measured value from said median. In place of the median, other statistical methods, such as the determination of quantiles (e.g. quartiles or percentiles) or mathematical models, preferably Cox Regression may be used analogously to the above description in order to obtain the above-mentioned reference value and/or otherwise determine the significance of a measured value with respect to the physiological status of a given subject from which the sample has been obtained. Said mathematical or statistical methods or models are well known to the person skilled in the art and the use thereof in the context of medicinal applications is well established.

The "term" biomarker (biological marker) relates to measurable and quantifiable biological parameters (e.g., specific enzyme concentration, specific hormone concentration, specific gene phenotype distribution in a population, presence of biological substances) which serve as indices for health- and physiology-related assessments, such as disease risk, psychiatric disorders, environmental exposure and its effects, disease diagnosis, metabolic processes, substance abuse, pregnancy, cell line development, epidemiologic studies, etc. Furthermore, a biomarker is defined as a characteristic that is objectively measured and evaluated as an indicator of normal biological processes, pathogenic processes, or pharmacologic responses to a therapeutic intervention, A biomarker may be measured on a biosample (as a blood, urine, or tissue test), it may be a recording obtained from a person (blood pressure, ECG, or Holter), or it may be an imaging test (echocardiogram or CT scan) (Vasan et al, 2006, Circulation 113:2335-2362).

Biomarkers can indicate a variety of health or disease characteristics, including the level or type of exposure to an environmental factor, genetic susceptibility, genetic responses to exposures, biomarkers of subclinical or clinical disease, or indicators of response to therapy. Thus, a simplistic way to think of biomarkers is as indicators of disease trait (risk factor or risk biomarker), disease state (preclinical or clinical), or disease rate (progression). Accordingly, biomarkers can be classified as antecedent biomarkers (identifying the risk of developing an illness), screening biomarkers (screening for subclinical disease), diagnostic biomarkers (recognizing overt disease), staging biomarkers (categorizing disease severity), or prognostic biomarkers (predicting future disease course, including recurrence and response to therapy, and monitoring efficacy of therapy). Biomarkers may also serve as surrogate end points. A surrogate end point is one that can be used as an outcome in clinical trials to evaluate safety and effectiveness of therapies in lieu of measurement of the true outcome of interest. The underlying principle is that alterations in the surrogate end point track closely with changes in the outcome of interest. Surrogate end points have the advantage that they may be gathered in a shorter time frame and with less expense than end points such as morbidity and mortality, which require large clinical trials for evaluation. Additional values of surrogate end points include the fact that they are closer to the exposure/intervention of interest and may be easier to relate causally than more distant clinical events. An important disadvantage of surrogate end points is that if clinical outcome of interest is influenced by numerous factors (in addition to the surrogate end point), residual confounding may reduce the validity of the surrogate end point. It has been suggested that the validity of a surrogate end point is greater if it can explain at least 50% of the effect of an exposure or intervention on the outcome of interest. For instance, a biomarker may be a protein, peptide or a nucleic acid molecule.

One of said prognostic biomarker(s) is preferably proBNP or fragments thereof in a sample obtained from said patient. More preferably, said fragment of proBNP is NT pro-BNP or BNP.

In a particular embodiment, the in vitro method farther comprises determining the level of one or more additional prognostic biomarkers in a sample obtained from said patient, and correlating both said level of procalcitonin or fragments thereof and said level of one or more additional prognostic biomarkers to said predisposition to a risk, whereby the combination of said level of procalcitonin or fragments thereof with said level of one or more additional prognostic biomarkers increases the predictive value of said level procalcitonin or fragments thereof for said risk.

The additional prognostic biomarker may for example be selected from a group comprising troponin, myeloperoxidase, CRP, neopterin, GDF-15, ST2, cystatin-C, as well as the following peptides in form of their mature peptides, prohormones (precursors) and associated prohormone fragments: natriuretic peptides, adrenomedullin, endothelins, vasopressin.

Preferably, the correlation between said level of procalcitonin or fragments thereof and said level of one or more additional prognostic biomarkers is conducted with a mathematical algorithm.

In a further aspect the present invention relates to the use of an ultrasensitive procalcitonin assay having a lower limit of detection of below about 0.05 ng/mL, preferably below about 0.04 ng/mL, more preferably below about 0.03 ng/mL, most preferably below about 0.02 ng/mL for determining in a patient having a primary disease not being an infection the risk of the patient to contact a further disease or medical condition which has not yet been manifested and/or is not yet symptomatic.

In a preferred embodiment of the use of the ultrasensitive procalcitortin assay, the level of procalcitonin or fragments thereof of at least 12 amino acids in length or a mixture of procalicitonin and/or fragments thereof, is determined in a sample from said patient. In one embodiment the level of only one fragment is determined. In another embodiment the level of a mixture of procalcitonin and/or fragments thereof is determined.

As mentioned herein, an "assay" or "diagnostic assay" can be of any type applied in the field of diagnostics, including but not restricted to assays methods based on enzymatic reactions, luminescence, fluorescence or radiochemicals. The preferred detection methods comprise rapid tests (point-of-care tests), radioimmunoassays, chemiluminescence- and fluorescence-immunoassays, Immunoblot assays, Enzyme-linked immunoassays (ELISA), Luminex-based bead arrays, and protein micro array assays. The assay types can further be microtitre plate-based, chip-based, bead-based, wherein the biomarkers can be attached to the surface or in solution. The assays can be homogenous or heterogeneous assays, sandwich assays, competitive and non-competitive assays. In a particularly preferred embodiment, the assay is in the form of a sandwich assay, which is a noncompetitive immunoassay, wherein the molecule to be detected and/or quantified is bound to a first antibody and to a second antibody. The first antibody may be bound to a solid phase, e.g. a bead, a surface of a well or other container, a chip or a strip, and the second antibody is an antibody which is labeled, e.g. with a dye, with a radioisotope, or a reactive or catalytically active moiety. The amount of labeled antibody on the site is then measured by an appropriate method. The general composition and procedures involved with "sandwich assays" are well-established and known to the skilled person (The Immunoassay Handbook, Ed. David Wild, Elsevier LTD, Oxford; 3rd ed, (May 2005), ISBN-13: 978-0080445267; Hultschig C et al., Curr Opin Chem Biol. 2006 February; 10(1):4-10. PMID: 16376134), incorporated herein by reference.

In a particularly preferred embodiment the assay comprises two capture molecules (capture probes), preferably antibodies which are both present as dispersions in a liquid reaction mixture, wherein a first marking component is attached to the first capture molecule, wherein said first marking component is part of a marking system based on fluorescence- or chemiluminescence-quenching or amplification, and a second marking component of said marking system is attached to the second capture molecule, so that upon binding of both capture molecules to the analyte to be detected, a measurable signal is generated that allows for the detection of the formed sandwich complexes in the solution comprising the sample.

In the context of the present invention, a capture probe may be selected from the group comprising a nucleic acid molecule, particularly an aptamer, a carbohydrate molecule, a PNA molecule, a protein, an antibody, a peptide, particularly a cyclic peptide or a glycoprotein.

Even more preferred, said marking system comprises rare earth cryptates or rare earth chelates in combination with a fluorescence dye or chemiluminescence dye, in particular a dye of the cyanine type.

In the context of the present invention, fluorescence based assays comprise the use of dyes, which may for instance be selected from the group comprising FAM (5- or 6-carboxyfluorescein), VIC, NED, Fluorescein, Fluoresceinisothiocyanate (FITC), IRD-700/800, Cyanine dyes, such as CY3, CY5, CY3.5, CY5.5, Cy7, Xanthen, 6-Carboxy-2',4',7',4,7-hexachlorofluorescein (HEX), TET, 6-Carboxy-4',5'-dichloro-2',7'-dimethodyfluorescein (JOE), N,N,N',N'-Tetramethyl-6-carboxyrhodamine (TAMRA), 6-Carboxy-X-rhodamine (ROX), 5-Carboxyrhodamine-6G (R6G5), 6-carboxyrhodamine-6G (RG6), Rhodamine, Rhodamine Green, Rhodamine Red, Rhodamine 110, BODIPY dyes, such as BODIPY TMR, Oregon Green, Coumarines such as Umbelliferone, Benzimides, such as Hoechst 33258; Phenanthridines, such as Texas Red, Yakima Yellow, Alexa Fluor, PET, Ethidiumbromide, Acridinium dyes, Carbazol dyes, Phenoxazine dyes, Porphyrine dyes, Polymethin dyes, and the like.

In the context of the present invention, chemiluminescence based assays comprise the use of dyes, based on the physical principles described for chemiluminescent materials in Kirk-Othmer, Encyclopedia of chemical technology, $4^{th}$ ed., executive editor, J. I. Kroschwitz; editor, M. Howe-Grant, John Wiley & Sons, 1993, vol. 15, p. 518-562, incorporated herein by reference, including citations on pages 551-562. Preferred chemiluminescent dyes are acridinium esters.

In the context of the present invention, the term "ultrasensitive procalcitonin assay" means that the assay for the detection of procalcitonin or fragments thereof and/or quantification of the level thereof has a lower limit of detection of below about 0.05 ng/mL, preferably below about 0.04 ng/mL, more preferably below about 0.03 ng/mL, most preferably below about 0.02 ng/mL.

An ultrasensitive PCT assay is for example the PCT sensitive LIA (Luminescence Immuno Assay) Kit (B.R.A.H.M.S AG, Hennigsdorf, Germany, Product No. 109.050). PCT levels in the context of the present invention may for example be determined with an assay as described above, preferably with the PCT sensitive LIA (Luminescence Immuno Assay) Kit (B.R.A.H.M.S AG, Hennigsdorf, Germany, Product No, 109,050) as in example 1 or following the general procedure described in example 2.

The use of an ultrasensitive procalcitonin assay is preferably for stratifying the risk for contracting a further disease or medical in a patient having a primary disease.

The ultrasensitive procalcitonin assay may be used for the control of the treatment or prevention of said further disease or medical condition. Preferably said treatment or prevention comprises administration of an antibiotic to the patient.

The ultrasensitive procalcitonin assay may for example be a sandwich assay comprising two antibodies against different moieties of procalcitonin.

In a particular embodiment of the use of the ultrasensitive procalcitonin assay, one antibody is against the calcitonin moiety of procalcitonin, and the other antibody is a monoclonal antibody against the katacalcin moiety of procalcitonin.

In the context of the present invention, the term "calcitonin moiety of procalcitonin" refers to a polypeptide comprising the amino acids 85-116 of pre-procalcitonin. In the context of the present invention, the "katacalcin moiety of procalcitonin" refers to a polypeptide comprising the amino acids 121-141 of pre-procalcitonin. The above amino acid numbers refer to the sequence of human pre-procalcitonin as listed in the Protein data bank entry on the world wide web at expasy.ch/uniprot/P01258. Also encompassed are amino acid sequences of analogous origin analogous in other species, as well as polypeptides with preferably, at least 90%, more preferably at least 95%, most preferably at least 98% sequence homology to the above-mentioned human polypeptides.

In yet another aspect the present invention relates to an antibiotic for the use in the treatment of a local infection for the prevention of a further disease or medical condition which has not yet been manifested in a patient having a primary disease, wherein said primary disease is not an infection and wherein the antibiotic is administered when the level of procalcitonin or fragments thereof of at least 12 amino acids in length, in a sample of the patient selected from the group comprising a blood sample, a serum sample and a plasma sample, is between 0.02 and 0.25 ng/mL, preferably between 0.02 and 0.1 ng/mL, Preferably, the risk of contracting a further disease or medical condition decreases when the said patient is treated with antibiotic.

In a further aspect the invention relates to an in vitro method for diagnosis of the presence of a bacterial infection in a patient, the method comprising: determining the level of procalcitonin or fragments thereof of at least 12 amino acids in length, in a sample obtained from said patient:
(i) at least once before the start of said antibiotic treatment or within six hours after the start of the treatment, and
(ii) at least once after 12 hours to 1 week after the start of an antibiotic treatment of the patient; and correlating said level of procalcitonin or fragments thereof to the presence of a bacterial infection, wherein a decrease of said level of at least 20% per 24 h ng/mL is indicative for the presence of a bacterial infection in the patient.

Preferably, the patient has a primary disease not being all infection and the level of procalcitonin or fragments thereof of at least 12 amino acids in length, in serum or plasma samples of said patient is below 0.25 ng/mL.

The term "antibiotic" in the context of the present invention refers to a chemical substance, which has the capacity to inhibit the growth of or to kill microorganisms, Different antibiotics may have various mechanism of action, e.g. by binding to bacterial ribosomal subunits, thereby inhibiting protein biosynthesis, inhibiting cell wall synthesis, e.g. by inhibiting peptidoglycan synthesis, interacting with the bacterial cytoplasmic membrane, thereby e.g. changing its permeability, inhibit bacterial DNA gyrase or topoisomerase IV enzyme, thereby inhibiting DNA replication and transcription, inhibiting folate synthesis, or inhibiting transcription by binding to RNA polymerase. The antibiotic in the context of the present invention may for example be selected from the group comprising β-Lactames, glykopeptides, polyketides, aminoglycoside antibiotics, polypeptide antibiotics, chinolones and sulfonamides. Preferably, the term refers to beta-lactam compounds like penicillines, cephalosporins or carbapenems; tetracyclines; macrolides; fluoroquinolones; sulphonamides; aminoglycosides; imidazoles; peptide-antibiotics and lincesamides More preferably, the term relates to amoxicillin, flucloxacillin, penicillin G, ampicillin, methicillin, oxacillin, cefoxitin, ceftriaxone, ceftrizoxime, imipenem, erythromacin, tylosin, tilmicosin, spiramycin, josamycin, azithromycin, clarithromycin, tetracycline, minocycline, doxycycline, lymecycline, norfloxacin, enoxacin, ofloxacin, co-trimoxazole, ciprofloxacin, trimethoprim, gentamicin, amikacin, metronidazole, bacitracin, clindamycin or lincomycin. Most preferably, the term relates to ampicillin, cefotaxime, erythromycin, tetracycline, ciprofloxacin, co-trimoxazole, gentamicin, metronidazole, bacitracin or clindomycin.

EXAMPLES

Example 1: Determination of Procalcitonin Levels in Samples of Patients with Various Primary Diseases 4997 consecutive blood sera samples of patients of a clinical lab have been analyzed to determine the level of procalcitonin (PCT) using the B.R.A.H.M.S PCT sensitive LIA (Luminescence Immuno Assay) Kit (B.R.A.H.M.S AG, Hennigsdorf, Germany, Product No. 109.050). The patients sera have been sent for analysis to the lab by different consulting specialist physicians from various medical fields, such as nephrology, urology, oncology, pediatrics, internal medicine, general medicine and others. The assay has been performed according to the manual shipped with the kit, except that the sample volume has been increased form 50 µL to 100 µL to increase the functional assay sensitivity (FAS) and to reliably determine the PCT concentrations in the lower concentration range (0.05 to 0.25 ng/mL).

Figure 2:
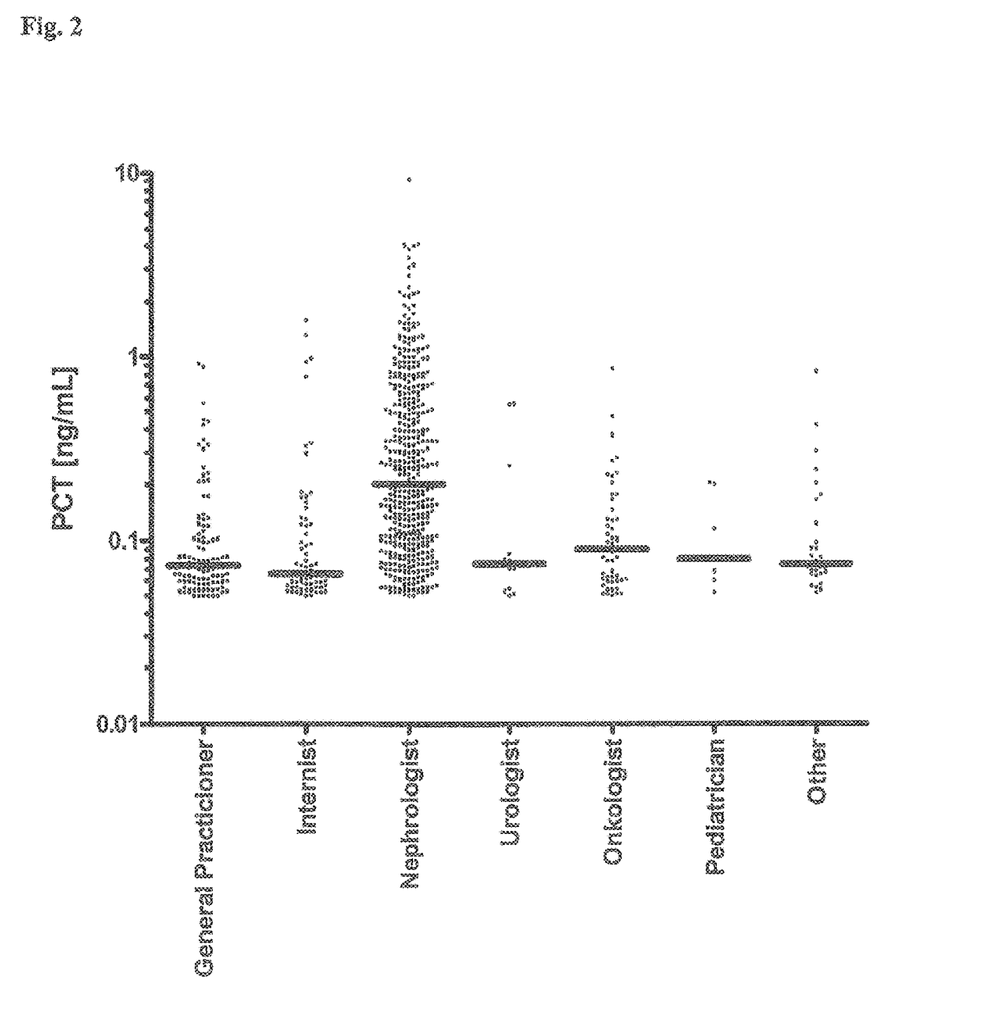
FIG. 2 shows the distribution of PCT levels above 0.05 ng/mL in relation the medical field of the consulting specialist physician who provided the respective sample. Medians in all groups are indicated.

The frequencies of the determined PCT levels have been plotted in a histogram (see appended FIG. 1). 66.7% of the sera samples showed PCT levels above 0.017 ng/mL, 26.0% of the sera samples showed PCT concentrations of above 0.03 ng/mL and 14.0% of the sera samples showed PCT levels of above 0.05 ng/mL. The samples having PCT concentrations above 0.05 ng/mL (i.e. 702 samples out of 4997 samples) have been classified according to the medical field of the consulting specialist physician from which the respective sample originated. This correlation is plotted in appended FIG. 2.

The high number of patients having a primary disease not being an infection but nevertheless having PCT levels above 0.03 ng/mL and 0.05 ng/mL, respectively, is a surprising finding.

Example 2: General Procedure for the Determination of Procalcitonin Levels in Samples of Patients Procalcitonin (PCT) can be measured as described (Morgenthaler N G et al.: Clin Chem, 2002 May, 48(5), 788-790), Sheep antibodies were raised against the calcitonin moiety of PCT, and a mouse monoclonal antibody was raised against the katacalcin moiety of PCT, Tubes were coated with the anti-katacalcin antibody. The anti-Calcitonin antibody was labelled with MACN Acridiniumester (InVent GmbH, Hennigsdorf, Germany) and served as tracer, Dilutions of recombinant PCT in normal horse serum served as standards. 100 µl sample or standard were incubated in the coated tubes for 30 minutes, 200 µl tracer were added. After incubation for 2 h the tubes were washed 4 times with 1 ml of LIA wash solution (B.R.A.H.M.S AG), and bound. Chemiluminescence was measured using a LB952T luminometer (Berthold, Germany).

The invention claimed is:
1. A method comprising administering an antibiotic to a patient:
wherein the patient has a primary disease not being an infection;
wherein, before administering of the antibiotic, the patient has had a level of analyte of procalcitonin or fragments thereof of at least 50 amino acids in length determined and the level of analyte of procalcitonin or fragments thereof of at least 50 amino acids in length determined is between 0.02 and 0.1 ng/mL.

2. A method comprising:
   determining a level of analyte of procalcitonin or fragments thereof of at least 50 amino acids in length in a patient;
   wherein the patient has a level of said analyte which is between 0.02 and 0.1 ng/mL; wherein the patient has a primary disease not being an infection; and
   after determining the level of analyte of procalcitonin or fragments thereof of at least 50 amino acids in length in the patient, administering an antibiotic to the patient.

3. A method according to claim 1, wherein the level of analyte of procalcitonin or fragments thereof of at least 50 amino acids in length in the patient being between 0.02 and 0.1 ng/mL correlates to a risk of the patient to contract a cardiological disease or condition which has not yet been manifested and/or is not yet symptomatic.

4. A method according to claim 1, wherein said primary disease is selected from cancer, diabetes, a chronic gastrointestinal disease, a chronic renal disease, hypertension, an orthopedic disease or a neurodegenerative disease.

5. The method according to claim 3, wherein said level of analyte of procalcitonin or fragments thereof of at least 50 amino acids in length being between 0.02 and 0.1 ng/mL is indicative for a bacterial infection in the patient, which may facilitate, accelerate and/or enhance the risk of the patient contracting or acquiring said cardiological disease or condition.

6. The method according to claim 5, wherein said bacterial infection is a local infection.

7. The method according to claim 3, wherein the risk of contracting the cardiological disease or condition decreases when said patient is treated with the antibiotic.

8. The method according to claim 3, wherein said further disease or condition is a cardiological disease or condition selected from the group consisting of atherosclerosis, acute coronary syndromes and heart failure.

9. The method according to claim 3, further comprising correlating said level of analyte of procalcitonin or fragments thereof of at least 50 amino acids in length with a level of one or more additional prognostic biomarkers, whereby a combination of said level of analyte of procalcitonin or fragments thereof of at least 50 amino acids in length with said level of additional prognostic biomarker(s) increases predictive value of said level of analyte of procalcitonin or fragments thereof or the level of said related marker for said risk.

10. The method according to claim 9, wherein one of said prognostic biomarker(s) is brain natriuretic peptide prohormone (proBNP) or a fragment thereof in a sample obtained from said patient.

11. The method according to claim 10, wherein said fragment of proBNP is a 76 amino acid N-terminal fragment of brain natriuretic peptide (NT proBNP) or brain natriuretic peptide (BNP).

12. A method according to claim 9, further comprising determining a level of one or more additional different prognostic biomarkers in a sample obtained from said patient, and correlating both said level of analyte of procalcitonin or fragments thereof and said level of one or more additional different prognostic biomarkers to said risk, whereby a combination of said level of analyte of procalcitonin or fragments thereof with said level of one or more additional different prognostic biomarkers increases predictive value of said level of analyte of procalcitonin or fragments thereof for said risk.

13. The method according to claim 12, wherein the additional different prognostic biomarker is selected from a group consisting of troponin, myeloperoxidase, CRP, neopterin, GDF-15, ST2, cystatin-C, and the following peptides in the form of their mature peptides, precursors, pro-hormones and associated prohormone fragments: natriuretic peptides, adrenomedullin, endothelins, and vasopressin.

14. A method according to claim 9, wherein the correlation between said level of analyte of procalcitonin or fragments thereof and said level of one or more additional prognostic biomarkers is conducted with a mathematical algorithm.

15. A method according to claim 12, wherein the correlation between said level of analyte of procalcitonin or fragments thereof and said level of one or more additional different prognostic biomarkers is conducted with a mathematical algorithm.

16. The method of claim 1, wherein, said level of analyte is between 0.03 and 0.1 ng/mL.

17. The method of claim 1, wherein, said level of analyte is between 0.05 and 0.1 ng/mL.

18. A method according to claim 2, wherein the level of analyte of procalcitonin or fragments thereof of at least 50 amino acids in length in the patient being between 0.02 and 0.1 ng/mL correlates to a risk of the patient to contract a cardiological disease or condition which has not yet been manifested and/or is not yet symptomatic.

19. A method according to claim 2, wherein said primary disease is selected from cancer, diabetes, a chronic gastrointestinal disease, a chronic renal disease, hypertension, an orthopedic disease or a neurodegenerative disease.

20. The method according to claim 18, wherein said level of analyte of procalcitonin or fragments thereof of at least 50 amino acids in length being between 0.02 and 0.1 ng/mL is indicative for a bacterial infection in the patient, which may facilitate, accelerate and/or enhance the risk of the patient contracting or acquiring said cardiological disease or condition.

21. The method according to claim 20, wherein said bacterial infection is a local infection.

22. The method according to claim 18, wherein the risk of contracting the cardiological disease or condition decreases when said patient is treated with the antibiotic.

23. The method according to claim 18, wherein said further disease or condition is a cardiological disease or condition selected from the group consisting of atherosclerosis, acute coronary syndromes and heart failure.

24. The method according to claim 18, further comprising correlating said level of analyte of procalcitonin or fragments thereof of at least 50 amino acids in length with a level of one or more additional prognostic biomarkers, whereby a combination of said level of analyte of procalcitonin or fragments thereof of at least 50 amino acids in length with said level of additional prognostic biomarker(s) increases predictive value of said level of analyte of procalcitonin or fragments thereof or the level of said related marker for said risk.

25. The method according to claim 24, wherein one of said prognostic biomarker(s) is brain natriuretic peptide prohormone (proBNP) or a fragment thereof in a sample obtained from said patient.

26. The method according to claim 25, wherein said fragment of proBNP is a 76 amino acid N-terminal fragment of brain natriuretic peptide (NT proBNP) or brain natriuretic peptide (BNP).

27. A method according to claim 24, further comprising determining a level of one or more additional different prognostic biomarkers in a sample obtained from said patient, and correlating both said level of analyte of procalcitonin or fragments thereof and said level of one or more additional different prognostic biomarkers to said risk, whereby a combination of said level of analyte of procalcitonin or fragments thereof with said level of one or more additional different prognostic biomarkers increases predictive value of said level of analyte of procalcitonin or fragments thereof for said risk.

28. The method according to claim 27, wherein the additional different prognostic biomarker is selected from a group consisting of troponin, myeloperoxidase, CRP, neopterin, GDF-15, ST2, cystatin-C, and the following peptides in the form of their mature peptides, precursors, pro-hormones and associated prohormone fragments: natriuretic peptides, adrenomedullin, endothelins, and vasopressin.

29. A method according to claim 24, wherein the correlation between said level of analyte of procalcitonin or fragments thereof and said level of one or more additional prognostic biomarkers is conducted with a mathematical algorithm.

30. A method according to claim 27, wherein the correlation between said level of analyte of procalcitonin or fragments thereof and said level of one or more additional different prognostic biomarkers is conducted with a mathematical algorithm.

31. The method of claim 2, wherein, said level of analyte is between 0.03 and 0.1 ng/mL.

32. The method of claim 2, wherein said level of analyte is between 0.05 and 0.1 ng/mL.

33. The method of claim 1, wherein the level of analyte of procalcitonin or fragments thereof of at least 50 amino acids in length was determined in a sample obtained from said patient selected from the group consisting of a blood sample, a serum sample, a plasma sample and an extract of any of the aforementioned samples, wherein said sample was contacted with a diagnostic assay antibody which specifically binds to the analyte, and a resulting antibody: analyte complex was detected and quantitated to determine the level of the analyte in the sample.

34. The method of claim 2, wherein the level of analyte of procalcitonin or fragments thereof of at least 50 amino acids in length is determined in a sample obtained from said patient selected from the group consisting of a blood sample, a serum sample, a plasma sample and an extract of any of the aforementioned samples, said sample being contacted with a diagnostic assay antibody which specifically binds to the analyte, and detecting and quantitating a resulting antibody: analyte complex, thereby determining the level of the analyte in the sample.

* * * * *